US 8,644,924 B2

(12) United States Patent
Shuros et al.

(10) Patent No.: US 8,644,924 B2
(45) Date of Patent: Feb. 4, 2014

(54) PREFERENTIAL MECHANICAL UNLOADING DURING ANTI-TACHYCARDIA PACING

(75) Inventors: Allan C. Shuros, St. Paul, MN (US); Barun Maskara, Blaine, MN (US); Shantha Arcot-Krishnamurthy, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 618 days.

(21) Appl. No.: 12/573,520

(22) Filed: Oct. 5, 2009

(65) Prior Publication Data

US 2010/0087881 A1 Apr. 8, 2010

Related U.S. Application Data

(60) Provisional application No. 61/103,024, filed on Oct. 6, 2008.

(51) Int. Cl.
*A61N 1/39* (2006.01)
(52) U.S. Cl.
USPC .................................. 607/4; 607/14
(58) Field of Classification Search
USPC .................................. 607/5, 4, 14
See application file for complete search history.

(56) References Cited

U.S. PATENT DOCUMENTS

| 6,141,588 | A * | 10/2000 | Cox et al. ................. 607/9 |
| 6,795,731 | B1 | 9/2004 | Kroll et al. |
| 6,885,890 | B2 | 4/2005 | Spinelli et al. |
| 7,313,438 | B2 | 12/2007 | Zhang |
| 2008/0200961 | A1 | 8/2008 | Kroll et al. |

OTHER PUBLICATIONS

"International Application Serial No. PCT/US2009/059699, International Search Report mailed Jan. 7, 2010", 4 pgs.
"International Application Serial No. PCT/US2009/059699, Written Opinion mailed Jan. 7, 2010", 7 pgs.
Lu, F., et al., "The effect of streptomycin on stretch-induced electrophysiological changes of isolated acute myocardial infarcted hearts in rats", *Europace*, 9, (2007), 578-584.

* cited by examiner

*Primary Examiner* — Niketa Patel
*Assistant Examiner* — Alyssa M Alter
(74) *Attorney, Agent, or Firm* — Schwegman Lundberg & Woessner, P.A.

(57) ABSTRACT

A pacing device and method for operating same is disclosed in which the point of origin of an arrhythmia is estimated in order to more provide more effective treatment. The origin of an arrhythmia may be estimated by analyzing the timing of electrical events as detected at different electrode sites and/or using different sensing vectors. Anti-tachycardia pacing (ATP) may then be delivered to the most appropriate location.

20 Claims, 2 Drawing Sheets

PREFERENTIAL MECHANICAL UNLOADING DURING ANTI-TACHYCARDIA PACING

CROSS-REFERENCE TO RELATED APPLICATION

This application claims the benefit of U.S. Provisional Application No. 61/103,024, filed on Oct. 6, 2008, under 35 U.S.C. §119(e), which is hereby incorporated by reference.

FIELD OF THE INVENTION

This invention pertains to methods and system for treating cardiac arrhythmias with anti-tachycardia pacing.

BACKGROUND

Tachyarrhythmias are abnormal heart rhythms characterized by a rapid heart rate, typically expressed in units of beats per minute (bpm). Examples of tachyarrhythmias include supraventricular tachycardias (SVT's) such as sinus tachycardia, atrial tachycardia (AT), and atrial fibrillation (AF). The most dangerous tachyarrhythmias, however, are ventricular tachycardia (VT) and ventricular fibrillation (VF). Ventricular rhythms occur when re-entry of a depolarizing wavefront in areas of the ventricular myocardium with different conduction characteristics becomes self-sustaining or when an excitatory focus in the ventricle usurps control of the heart rate from the sinoatrial node. The result is rapid and ineffective contraction of the ventricles out of electromechanical synchrony with the atria. Most ventricular rhythms exhibit an abnormal QRS complex in an electrocardiogram because they do not use the normal ventricular conduction system, the depolarization spreading instead from the excitatory focus or point of re-entry directly into the myocardium. Ventricular tachycardia is typically characterized by distorted QRS complexes that occur at a rapid rate, while ventricular fibrillation is diagnosed when the ventricle depolarizes in a chaotic fashion with QRS complexes of constantly changing shape. Both ventricular tachycardia and ventricular fibrillation are hemodynamically compromising, and both can be life-threatening. Ventricular fibrillation, however, causes circulatory arrest within seconds and is the most common cause of sudden cardiac death.

Cardioversion (an electrical shock delivered to the heart synchronously with the QRS complex) and defibrillation (an electrical shock delivered without synchronization to the QRS complex to terminate ventricular fibrillation) can be used to terminate most tachyarrhythmias, including SVT's, VT, and VF. The electric shock terminates the tachyarrhythmia by depolarizing all of the myocardium simultaneously and rendering it refractory. A class of cardiac rhythm management devices known as an implantable cardioverter/defibrillator (ICD) provides this kind of therapy by delivering a shock pulse to the heart when the device detects fibrillation.

Another type of electrical therapy for tachycardia is anti-tachycardia pacing (ATP). In ATP, the heart is competitively paced with one or more pacing pulses in an effort to interrupt the reentrant circuit causing the tachycardia. ATP can be applied to either the ventricles or the atria. Modern ICD's typically have ATP capability so that ATP therapy is delivered to the heart when a tachycardia is detected, while a shock pulse is delivered when fibrillation occurs. Although cardioversion/defibrillation will terminate tachycardia, it consumes a large amount of stored power from the battery and results in patient discomfort owing to the high voltage of the shock pulses. It is desirable, therefore, for the ICD to use ATP to terminate a tachyarrhythmia whenever possible. It is commonly believed that only cardioversion/defibrillation will terminate fibrillation and certain high rate tachycardias, while ATP can be used to treat lower rate tachycardias. A tachyarrhythmia that is regarded as terminable by ATP therapy, based upon rate or other factors, will be referred to herein as either a terminable tachyarrhythmia or a tachycardia.

In most ICD's with ATP capability, fibrillation (VF or AF) is distinguished from tachycardia (VT or AT) using rate-based criteria so that ATP or shock therapy can be delivered as appropriate. The ventricular heart rate is usually measured by detection of the time between successive R waves (i.e., ventricular depolarizations), and the atrial rate is measured by detection of the time between successive P waves (atrial depolarizations). A measured heart rate is classified as a tachycardia when the rate is in a tachycardia zone, defined as a range of rates above a tachycardia detection rate (TDR) but below a fibrillation detection rate (FDR). A measured heart rate above the FDR, on the other hand, is in the fibrillation zone and is classified as either atrial or ventricular fibrillation. In a typical device, a tachyarrhythmia with a heart rate in the tachycardia zone is treated with ATP therapy in order to avoid an unnecessary painful shock to the patient, and a defibrillation shock is delivered if the pacing fails to terminate the tachyarrhythmia. The present disclosure relates to a method and apparatus for delivering ATP therapy in a manner that increases the likelihood that ATP therapy will terminate a tachyarrhythmia without resorting to a defibrillation shock.

DETAILED DESCRIPTION

Figure 1:
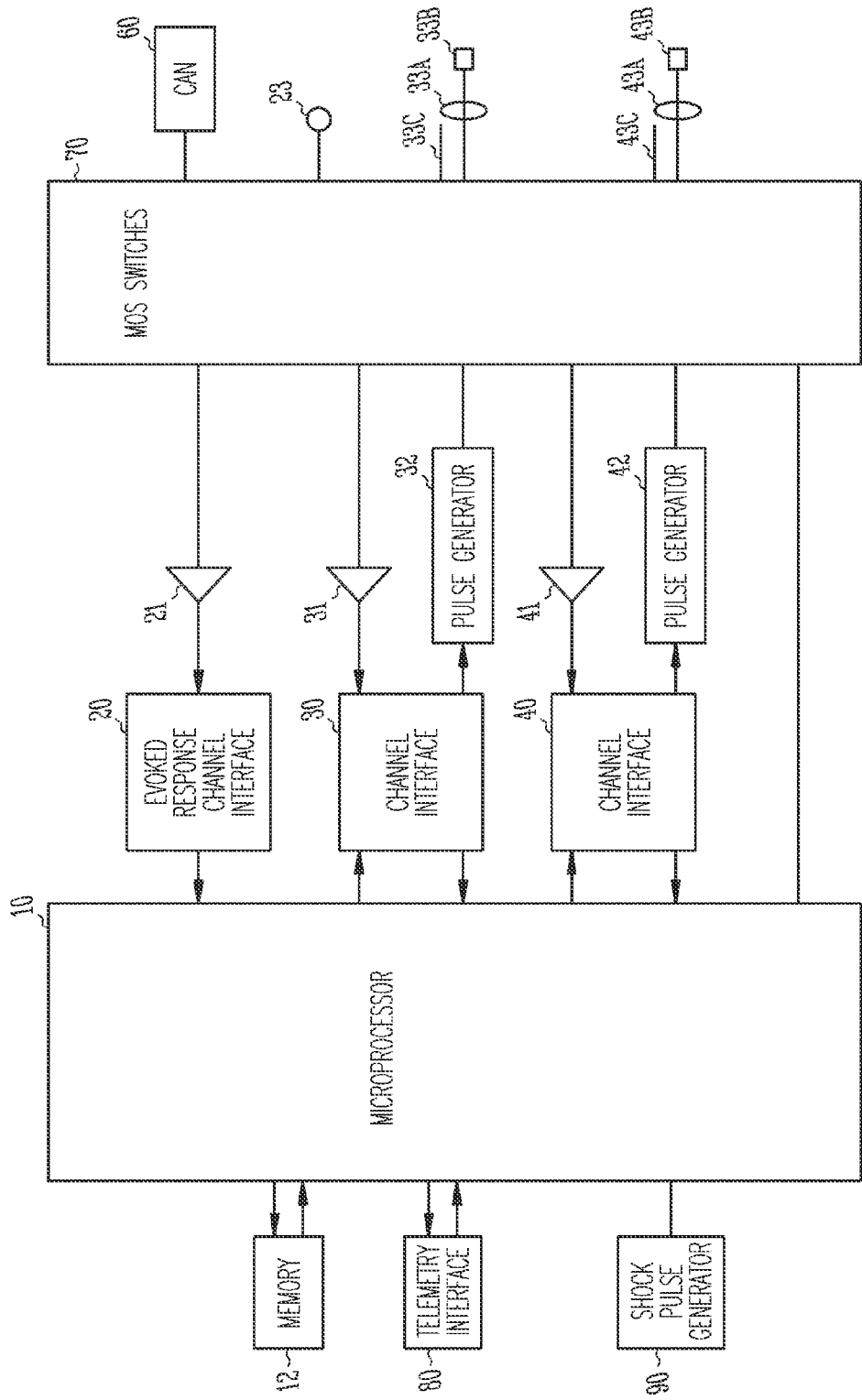
FIG. 1 is a block diagram of a cardiac rhythm management device with ATP and cardioversion/defibrillation capability.

The mechanism by which ATP therapy converts a tachyarrhythmia is through the entrainment of the heart by a burst of pacing pulses which results in the termination of the tachyarrhythmia. Entrainment of the heart means that a plurality of consecutive ATP pulses have succeeded in capturing the heart. When this occurs, the ATP burst has penetrated into the abnormal re-entrant cycles and is thus able to restore a normal pattern of excitation.

Although ATP has been demonstrated to be very effective at treating atrial and ventricular tachycardias, the therapy is not always effective. One factor that may adversely affect the effectiveness of ATP in certain situations is how close the origin of the arrhythmia is to the ATP pacing site. When a heart chamber is excited with a pacing pulse, the wave of excitation conducts through the myocardium and spreads from the pacing site to cause progressive myocardial contraction. This is in contrast to a normal heart beat in which the excitation spreads throughout the myocardium via the heart's specialized conduction system which has a significantly faster conduction time. The result is that a paced heart beat is more asynchronous than a normal heart beat with myocardial regions close to the pacing site contracting earlier than more remote regions. The later contracting regions more remote from the pacing site are stretched by the earlier contracting regions (i.e., are subjected to an increased pre-load) and then contract against a higher systolic pressure than the earlier contracting regions (i.e., are subjected to an increased afterload). The increased myocardial stretch brought about by later contraction during systole can modulate a myocardial region's electrophysiological characteristics. Such changes may include shortening of both the action potential duration and the effective refractory period, production of after-depolarizations and triggered activity, a decrease in early repolarization, and an increase in late repolarization. If a pace is delivered to a region remote to the point of origin of an arrhythmia, therefore, an increased stretch is imparted to the arrhythmic region, thereby enhancing the arrhythmogenic substrate.

Described herein is a pacing device and method for operating same in which the point of origin of an arrhythmia is estimated in order to more provide more effective treatment. The origin of an arrhythmia may be estimated by analyzing the timing of electrical events as detected at different electrode sites and/or using different sensing vectors. The device may use a plurality of electrodes incorporated in separate leads or in multi-polar leads for this purpose. For example, a far-field electrogram may be generated during a tachyarrhythmia using a unipolar electrode (e.g., the shock electrode or a subcutaneous electrode), where the time at which an atrium or ventricle is first activated can be determined as the time of the initial amplitude change. Which of the paired atria or ventricles is activated first as represented in the far-field electrogram can be determined from the times at which senses occur in bipolar sensing channels employing electrodes disposed in the different heart chambers. After determining which heart chamber contains the arrhythmic origin, the time of activation as determined from the far-field electrode may then be used as a fiducial point for estimating the distance from the arrhythmic point of the electrode or electrodes located in the arrhythmic chamber. The direction of the arrhythmic wave propagation can also be determined using the timings of sensing at different electrode sites.

After determination as to which of the available pacing electrodes is closest to the arrhythmia origin, the device may be configured to deliver ATP pacing pulses to a single site (or multiple sites) closest to the region of arrhythmia origination in order to unload (not stretch) that specific region. Electronic repositioning may be used to strategically place the pacing vector closest to arrhythmia origin. The device may also select between an extended bipolar versus a dedicated bipolar pacing configuration (e.g., widely spaced versus closely spaced electrodes). For example, an atrial lead with additional poles and a biased lead body may be used for site-selected ATP and preferential unloading pacing of an atrium depending on the site of an atrial arrhythmia. An LV coronary sinus lead with basal electrodes could be used, for example, to sense LA activity and direct ATP therapy if the arrhythmia originates in LA (e.g., using an LV CS to RA tip vector). Alternatively, epicardial electrodes may be placed on the atria or ventricles for more precise monitoring/therapy.

U.S. Pat. Nos. 7,313,438 and 6,885,890 (both assigned to Cardiac Pacemakers, Inc. and hereby incorporated by reference) describe the delivery of ATP pacing to the heart chamber deemed to be where the tachyarrhythmia originates. The device described herein, however, may be configured to determine which one or ones of a plurality of possible pacing electrodes located within a single heart chamber are closest to the arrhythmia origination point and then deliver ATP pacing using that electrode or electrodes. The device may additionally be configured to estimate the distance from the arrhythmia origination point for different possible pacing electrodes and compare the closest such estimated distance to some predetermined threshold distance. If no pacing electrode is located within the threshold distance to the arrhythmia origination point, the device may be configured to not deliver ATP therapy. The device may be configured to deliver another therapy such as a cardioversion or defibrillation shock instead in order to terminate the arrhythmia. An arrhythmia mapping study may also be performed at the time of implant to estimate at-risk sites for arrhythmia origin. Such information would aid in strategic placement of sensing/pacing electrodes. If all identified arrhythmia origin sites are far from any pacing electrode site, the device may be configured to not deliver ATP therapy.

1. Hardware Platform

FIG. 1 is a system diagram of a microprocessor-based cardiac rhythm management device with the capability of delivering cardioversion/defibrillation shocks as well as delivering anti-tachycardia pacing therapy to either the ventricles or the atria. The device may also be configured to deliver conventional (e.g., bradycardia) pacing as well. Such devices are usually implanted subcutaneously on the patient's chest and connected to electrodes by leads threaded through the vessels of the upper venous system into the heart. An electrode can be connected to a sensing channel that generates an electrogram signal representing cardiac electrical activity at the electrode site and/or connected to a pacing or shocking channel for delivering pacing or shock pulses to the site.

A block diagram of an implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external programmer or other device via a wireless telemetry link.

The device shown in FIG. 1 has two sensing/pacing channels, where a pacing channel is made up of a pulse generator connectable to an electrode while a sensing channel is made up of the sense amplifier connectable to an electrode. (As the terms are usually used, a sensing channel or pacing channel may be taken to mean either the physical components that actually make up the channel while in use such as the pulse generation or sensing circuitry together with the electrodes connected thereto or may be taken to mean only the pulse generation circuitry or sensing circuitry together with appropriate output or input ports for connecting to electrodes. Unless indicated otherwise, the latter definition will be used herein.) A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. In an example configuration, one sensing/pacing channel is made up of sense amplifier 41, pulse generator 42, and a channel interface 40 that can be connected to ring electrode 43a and tip electrode 43b of bipolar lead 43c, while another sensing/pacing channel is made up of sense amplifier 31, pulse generator 32, and a channel interface 30 that can be connected to ring electrode 33a and tip electrode 33b of bipolar lead 33c. The channels may be configured as either atrial or ventricular channels depending upon the location of the electrode to which they are connected. A dedicated evoked response sensing channel is also shown made up of a channel interface 20 and sense amplifier 21 that can be connected to electrode 23. The switch matrix may switch the input of the evoked response channel to the electrode 23 referenced to the device housing 60 or to any of the available electrodes so that an evoked response may be detected in either the atria or the ventricles.

The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator 90 is interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense when a sense signal (i.e., a voltage sensed by an electrode representing cardiac electrical activity, sometimes called an electrogram signal) generated by a particular channel exceeds a specified intrinsic detection threshold. A chamber sense may be either an atrial sense or a ventricular sense depending on whether it occurs in the atrial or ventricular sensing channel. Pacing algorithms used in particular pacing modes employ such senses to trigger or inhibit pacing. Both bradycardia and anti-tachycardia pacing modes may be implemented in code executed by the controller.

2. Anti-Tachycardia Pacing

The cardiac rhythm management device of FIG. 1 may be programmed with a plurality of selectable ATP pacing protocols that define the manner in which anti-tachycardia pacing is delivered. In a microprocessor-based device, the output of pacing pulses is controlled by a pacing routine that implements the selected pacing protocol as defined by various parameters. A data structure stored in memory contains the parameter sets that define each of the available pacing protocols. Pacing protocols for ATP therapy attempt to block the reentrant depolarization wavefront causing the tachycardia with depolarizing wavefronts produced by a burst of pacing pulses. (A burst, as the term is used herein, may consist of one or more pacing pulses.) Protocols may vary according to parameters that define the number of pulses delivered and the particular timing employed. For example, the protocol may define a burst of pulses delivered at a specified pacing interval (or with varying pacing intervals) and for a specified time. The protocol may further define the duration and amplitude of the pacing pulses. Different protocols are apt to be more successful than others in terminating particular tachyarrhythmias that may differ as to rate and/or depolarization pattern.

For this reason, modern cardiac rhythm management devices are capable of employing a number of different ATP protocols to deliver therapy.

The device delivers ATP therapy or a defibrillation shock under programmed control of the microprocessor in response to sensed activity from the sensing channels. A sensing routine analyzes the electrical activity received from the sensing channels in order to detect a tachyarrhythmia, and the tachyarrhythmia is then classified as a tachycardia (i.e., a terminable tachyarrhythmia) or fibrillation based upon rate and/or other criteria. The device detects a ventricular tachyarrhythmia, for example, by counting ventricular senses received via the ventricular sensing channel in order to measure the heart rate and determine whether the rate exceeds a selected threshold value. An atrial tachyarrhythmia is similarly detected via an atrial sensing channel. Once a tachyarrhythmia is detected, the rhythm is classified into either a tachycardia or a fibrillation zone by comparing the heart rate to a fibrillation rate boundary or by other means such as assessing the stability of the rhythm. If the tachyarrhythmia is classified as terminable, a pacing routine executed by the microprocessor delivers ATP pulses in accordance with the parameters of a selected protocol. In an exemplary embodiment, the device is programmed to deliver a burst of ATP pulses in accordance with a predetermined protocol after detecting a terminable tachyarrhythmia. The burst could be, for example, a fixed programmable number N of pulses (e.g., 8) each separated by a specified pacing interval or a ramp-type burst in which the pacing interval varies during the burst. The burst is delivered after a specified coupling interval following a sense in the heart chamber in which the tachyarrhythmia is occurring.

In an exemplary embodiment, a pacing device includes a plurality of electrodes adapted for disposition at cardiac locations and a controller programmed for connecting selected electrodes to sensing channels for generating an electrogram signal from an electrode location or pacing channels for delivering pacing pulses to an electrode location. The controller is programmed to detect a tachyarrhythmia when a rate at which senses are detected in a sensing channel exceeds a tachyarrhythmia threshold value. ATP is delivered by the pacing device after detection of a tachycardia by: 1) estimating the location of an arrhythmia (i.e., a tachyarrhythmia) origination point for the tachycardia from sense signals generated by a plurality of sensing channels, 2) estimating the distance from the arrhythmia origination point of each of a plurality of available pacing electrodes, 3) configuring a pacing channel with a pacing electrode determined to the closest to the arrhythmia origination point, and 4) delivering ATP therapy via the configured pacing channel. The plurality of available pacing electrodes may include a plurality of electrodes disposed in a single heart chamber, in different heart chambers, in a ventricle, or in an atrium. The device may also be configured to compare the distances from the arrhythmia origination point of the plurality of available pacing electrodes with a predetermined threshold distance and choose to not deliver ATP therapy if none of the distances are within the predetermined threshold distance of the arrhythmia origination point. If none of the distances are within the predetermined threshold distance of the arrhythmia origination point, the device may deliver shock therapy to treat the tachycardia. The distance from the arrhythmia origination point of each of the plurality of available pacing electrodes may be from a plurality of bipolar sense signals and a far-field sense signal.

Figure 2:
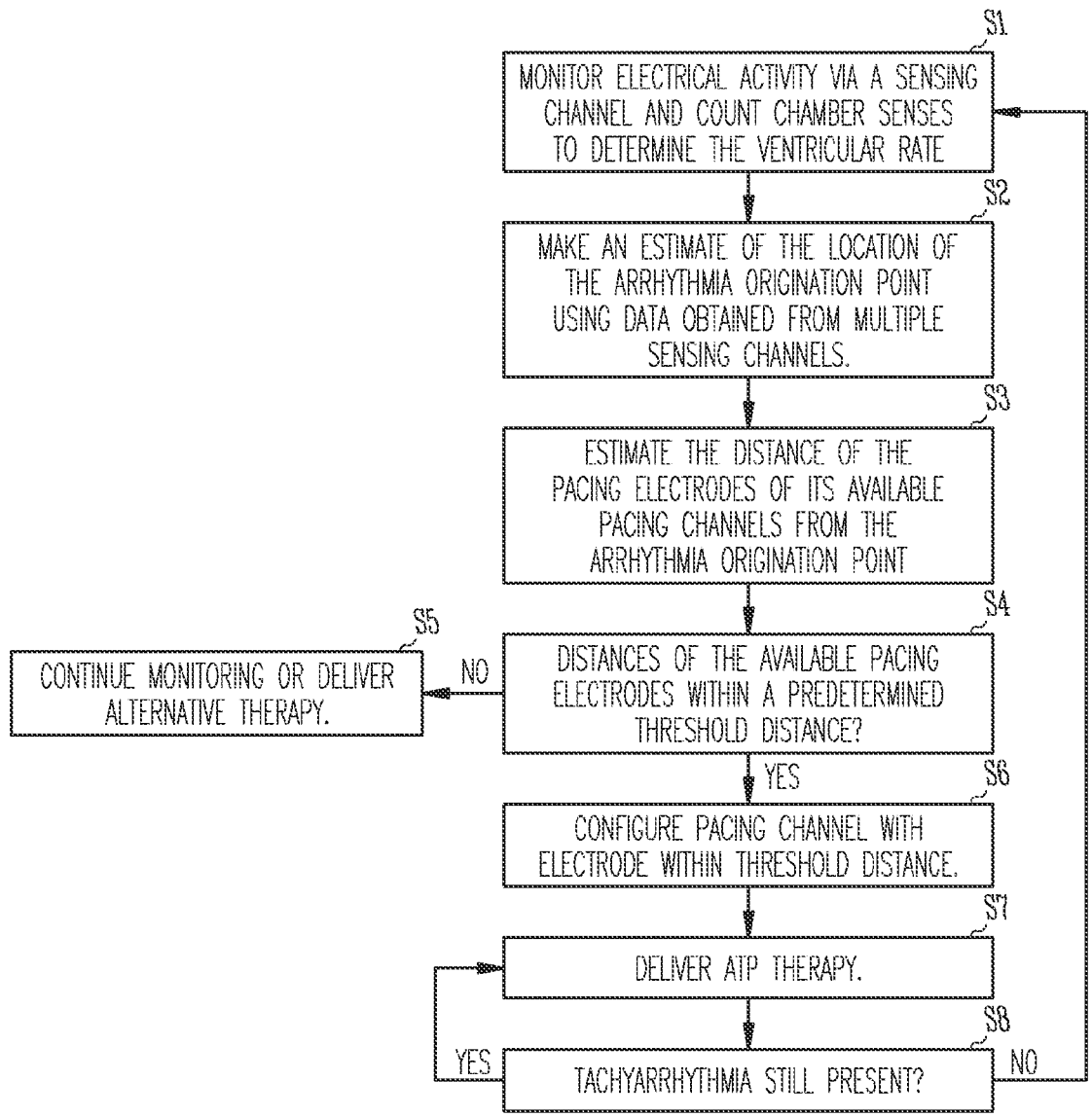
FIG. 2 is a flow diagram showing the steps performed in a particular implementation.

FIG. 2 is a flow diagram showing the steps performed by a cardiac rhythm management device in one particular algorithm for delivering ATP therapy to the ventricles in which the location of the point of origin of a detected arrhythmia is estimated. Other embodiments could be similarly configured to deliver ATP therapy to the atria. At state S1, the device begins monitoring electrical activity in a heart chamber via a sensing channel and counts chamber senses to determine the ventricular rate. Using a rate-based criterion, the rate is classified as a terminable tachyarrhythmia when it falls within a specified zone. If a terminable tachyarrhythmia is detected at state S1, the device prepares to deliver ATP therapy. At state S2, the device makes an estimate of the location of the arrhythmia origination point using data obtained from multiple sensing channels. At state S3, the device estimates the distance of the pacing electrodes of its available pacing channels from the arrhythmia origination point. At state S4, the distances of the available pacing electrodes are compared with a predetermined threshold distance. If no available pacing electrodes are within the threshold distance to the arrhythmia origin, the device is configured to exit to state S5 to either delivery another type of therapy (e.g., shock therapy) or to continue monitoring and deliver shock therapy if conditions warrant. If one or more available pacing electrodes are within the threshold distance, the device configures a pacing channel with the electrode at state S6 and delivers ATP therapy using that pacing channel at state S7. At state S8, ventricular activity is monitored to see whether or not the tachyarrhythmia is still present. If so, the device returns to state S7 to continue delivering ATP therapy. If not, the device returns to state S1 to continue monitoring.

As described above, a pacing device may be configured to determine the origin of a tachyarrhythmia from electrical activity sensed by its sensing channels. In another embodiment, a device may use mechanical strain to determine arrhythmia location. Multiple leads each incorporate a mechanical sensor (e.g., a strain-optical, piezoelectric, or accelerometer sensor) that detects origin of activation. A lead located near the arrhythmia origin area will then move before the remote lead. ATP is then applied to the lead within the area of arrhythmia origin.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A method for delivery of anti-tachycardia pacing (ATP) therapy by a cardiac rhythm management device after detection of a tachycardia, comprising:
   determining an activation time for the tachycardia from an initial amplitude change of a far-field electrogram;
   determining when senses occur at a plurality of available pacing electrodes configured into sensing channels and estimating the distance from each of the electrodes to an arrhythmia origination point using the activation time as a fiducial point;
   configuring a pacing channel with a pacing electrode determined to be closest to the arrhythmia origination point; and,
   delivering ATP therapy via the configured pacing channel.

2. The method of claim 1 further comprising:
   comparing the distances from the arrhythmia origination point of the plurality of available pacing electrodes with a predetermined threshold distance;
   choosing to not deliver ATP therapy if none of the distances are within the predetermined threshold distance of the arrhythmia origination point.

3. The method of claim 2 further comprising delivering shock therapy to treat the tachycardia if none of the distances are within the predetermined threshold distance of the arrhythmia origination point.

4. The method of claim 1 further comprising estimating the distance from the arrhythmia origination point of each of a plurality of available pacing electrodes from a plurality of bipolar electrogram signals and a far-field electrogram signal.

5. The method of claim 4 wherein the far-field electrogram signal is generated with a sensing channel that includes a shock electrode.

6. The method of claim 4 wherein the far-field electrogram signal is generated with a sensing channel that includes a subcutaneous electrode.

7. The method of claim 1 wherein the plurality of available pacing electrodes includes a plurality of electrodes disposed in a single heart chamber.

8. The method of claim 1 wherein the plurality of available pacing electrodes includes a plurality of electrodes disposed in different heart chambers.

9. The method of claim 1 wherein the plurality of available pacing electrodes includes a plurality of electrodes disposed in an atrium.

10. The method of claim 1 wherein the plurality of available pacing electrodes includes a plurality of electrodes disposed in a ventricle.

11. A cardiac rhythm management device, comprising:
    one or more sensing amplifiers and one or more pulse generators for incorporation into sensing and pacing channels, respectively;
    a controller programmed for configuring sensing and/or pacing channels with selected electrodes;
    wherein the controller is programmed to detect a tachyarrhythmia when a rate at which senses are detected in a sensing channel exceeds a tachyarrhythmia threshold value; and
    wherein, when a tachyarrhythmia is detected, the controller is further programmed to:
    determine an activation time for the tachyarrhythmia from an initial amplitude change of a far-field electrogram;
    determine when senses occur at a plurality of available pacing electrodes configured into sensing channels and estimate the distance from each of the electrodes to an arrhythmia origination point using the activation time as a fiducial point;
    configure a pacing channel for delivering ATP therapy with a pacing electrode determined to be the closest to the arrhythmia origination point and deliver ATP therapy via the pacing channel.

12. The device of claim 11 wherein the controller is further programmed to:
    compare the distances from the arrhythmia origination point of the plurality of available pacing electrodes with a predetermined threshold distance;
    choose to not deliver ATP therapy if none of the distances are within the predetermined threshold distance of the arrhythmia origination point.

13. The device of claim 12 wherein the controller is further programmed to deliver shock therapy to treat the tachycardia if none of the distances are within the predetermined threshold distance of the arrhythmia origination point.

14. The device of claim 11 wherein the controller is further programmed to estimate the distance from the arrhythmia origination point of each of a plurality of available pacing electrodes from a plurality of bipolar electrogram signals and a far-field electrogram signal.

15. The device of claim 14 wherein the far-field electrogram signal is generated with a sensing channel connected to a shock electrode.

16. The device of claim 14 wherein the far-field electrogram signal is generated with a sensing channel connected to a subcutaneous electrode.

17. The device of claim 11 wherein the plurality of available pacing electrodes includes a plurality of electrodes adapted for disposition in a single heart chamber.

18. The device of claim 11 wherein the plurality of available pacing electrodes includes a plurality of electrodes adapted for disposition in different heart chambers.

19. The device of claim 11 wherein the plurality of available pacing electrodes includes a plurality of electrodes adapted for disposition in an atrium.

20. The device of claim 11 wherein the plurality of available pacing electrodes includes a plurality of electrodes adapted for disposition in a ventricle.

* * * * *